(12) United States Patent
Hill

(10) Patent No.: US 7,985,871 B2
(45) Date of Patent: *Jul. 26, 2011

(54) PREPARATION OF TETRAKIS[3(3,5-DI-TERT-BUTYL-4-HYDROXYPHENYL)PROPIONYL OXYMETHYL]METHANE

(75) Inventor: Jonathan S. Hill, Manchester (GB)

(73) Assignee: Chemtura Corporation, Middlebury, CT (US)

( * ) Notice: Subject to any disclaimer, the term of this patent is extended or adjusted under 35 U.S.C. 154(b) by 19 days.

This patent is subject to a terminal disclaimer.

(21) Appl. No.: 12/536,853

(22) Filed: Aug. 6, 2009

(65) Prior Publication Data

US 2010/0036151 A1 Feb. 11, 2010

Related U.S. Application Data

(63) Continuation of application No. 10/577,186, filed as application No. PCT/GB2004/004546 on Oct. 27, 2004, now Pat. No. 7,601,862.

(30) Foreign Application Priority Data

Oct. 27, 2003 (GB) .................................. 0324964.6

(51) Int. Cl.
*C07C 67/03* (2006.01)
*C07C 69/732* (2006.01)

(52) U.S. Cl. ......................................................... 560/55
(58) Field of Classification Search ........................ None
See application file for complete search history.

(56) References Cited

U.S. PATENT DOCUMENTS 7,601,862 B2 * 10/2009 Hill ................................. 560/55

* cited by examiner

*Primary Examiner* — Daniel Sullivan
*Assistant Examiner* — Yevegeny Valenrod
(74) *Attorney, Agent, or Firm* — Joseph Suhadolnik

(57) ABSTRACT

A transesterification process for the preparation of tetrakis[3-(3,5-di-tert-butyl-4-hydroxy phenyl)propionyl oxymethyl] methane by the reaction of methyl-(3,5-di-tert-butyl-4-hydroxy phenyl)propionate ester with pentaerythritol wherein the reaction takes place in the presence of an ester exchange catalyst combination consisting of (a) at least one basic or neutral catalyst and (b) at least one metal compound capable of behaving as a Lewis acid being different from the basic or neutral catalyst and wherein the reaction is conducted through a first stage in which only the at least one basic or neutral catalyst is present in the reaction mixture followed by a second stage which commences with the addition of Lewis acid catalyst to the reaction mixture when the amount of di-substituted intermediate product contained within the reaction mixture has been reduced to less than 20 area % analysed by HPLC.

14 Claims, No Drawings

PREPARATION OF TETRAKIS[3(3,5-DI-TERT-BUTYL-4-HYDROXYPHENYL)PROPIONYL OXYMETHYL]METHANE

This application is a continuation application of copending U.S. patent application Ser. No. 10/577,186, entitled "PREPARATION OF TETRAKIS[3-(3,5-DI-TERT-BUTYL-4-HYDROXYPHENYL)PROPIONYL OXYMETHYL]METHANE," which is a national stage application of PCT Application No. PCT/GB2004/004546, filed Oct. 27, 2004, which claims priority to Great Britain Patent Application No. 0324964.6, filed on Oct. 27, 2003. Each of these documents are incorporated herein by reference in its entirety.

This invention relates to a process for the preparation of the sterically hindered hydroxyphenyl carboxylic acid ester tetrakis[3-(3,5-di-tert-butyl-4-hydroxy phenyl)propionyl oxymethyl]methane.

More particularly, this invention relates to a process for the preparation of tetrakis[3-(3,5-di-tert-butyl-4-hydroxy phenyl)propionyl oxymethyl]methane by the reaction of methyl-(3,5-di-tert-butyl-4-hydroxy phenyl)propionate with pentaerythritol in the presence of a catalyst system.

Tetrakis[3-(3,5-di-tert-butyl-4-hydroxy phenyl)propionyl oxymethyl]methane is an important commercial antioxidant. For example, it protects organic materials, such as plastics and lubricants, against thermal, oxidative and/or actinic degradation. There continues to be a need for tetrakis[3-(3,5-di-tert-butyl-4-hydroxy phenyl)propionyl oxymethyl]methane for use as an antioxidant and for improved processes for its preparation.

Due to toxicity concerns, there is a strong demand for the elimination of tin and especially organotin catalyst residues commonly used in the manufacture of phenolic antioxidants of the general class of sterically hindered hydroxyphenyl carboxylic acid esters e.g. tetrakis[3-(3,5-di-tert-butyl-4 hydroxy phenyl)propionyl oxymethyl]methane (which is manufactured by Great Lakes Chemical Corporation under the trade mark Anox 20). The use of lithium compounds as catalysts in the process of preparation also is well known but suffers from a number of problems, namely: (i) deactivation of the active lithium catalyst over time (ii) low reaction rate, particularly towards the end of the reaction and (iii) discolouration of the reaction mixture. The use of a more basic active catalyst to improve conversion rate leads to worse colour, whereas the use of a less basic catalyst gives better colour but slow conversion rate. Deactivation can be offset partially by dosing the catalyst, but this entails additional process steps, higher catalyst loadings and risk of more colour and other by-products.

It is also known that Lewis acid catalysts such as zinc salts can be used successfully for the preparation of sterically hindered hydroxyphenyl carboxylic acid esters from simple alcohols such as octadecanol to give octadecyl 3-(3',5'-di-t-butyl-4'-hydroxyphenyl)propionate but either fail entirely or are very slow for the reaction with a polyol such as pentaerythritol as used in the manufacture of tetrakis[3-(3,5-di-tert-butyl-4-hydroxy phenyl)propionyl oxymethyl]methane. The reason for the slow reaction in the case of pentaerythritol is explained in considerable detail later in this specification.

We have discovered that the manufacture of tetrakis[3-(3,5-di-tert-butyl-4-hydroxy phenyl)propionyl oxymethyl] methane by the reaction of methyl-(3,5-di-tert-butyl-4-hydroxy phenyl)propionate with pentaerythritol using a synergistic catalyst combination of (a) certain basic and neutral catalysts with (b) certain Lewis acid catalysts can overcome the above mentioned disadvantages of basic catalysts and Lewis acid catalysts when used separately as in the prior art.

According to the present invention, there is provided a transesterification process for the preparation of tetrakis[3-(3,5-di-tert-butyl-4-hydroxy phenyl)propionyl oxymethyl] methane by the reaction of methyl-(3,5-di-tert-butyl-4-hydroxy phenyl)propionate ester with pentaerythritol wherein the reaction takes place in the presence of an ester exchange catalyst combination consisting of (a) at least one basic or neutral catalyst and (b) at least one metal compound capable of behaving as a Lewis acid and wherein the reaction is conducted through a first stage in which only basic or neutral catalyst is present in the reaction mixture followed by a second stage which commences with the addition of Lewis acid catalyst to the reaction mixture when the amount of di-substituted intermediate product contained within the reaction mixture is less than 20 area % analysed by HPLC.

Preferably, the Lewis acid is added to the intermediate reaction mixture when the amount of di-substituted intermediate product contained within the reaction mixture is less than 10 area %, preferably 5 to 7 area %.

Preferably, the basic or neutral catalyst is lithium hydroxide, lithium hydroxide monohydrate, lithium methoxide, lithium hydride, lithium acetate or lithium amide, most preferably lithium hydroxide and lithium hydroxide monohydrate.

Preferably, the metal compound capable of behaving as a Lewis acid catalyst is a compound of a group Ib metal, a group IIa metal, a group IIb metal, a group IIIb metal, a group IVb metal, a group Vb metal, a transition metal, a lanthanide or an actinide.

Further preferably, the Lewis acid catalyst is zinc octanoate, zinc acetylacetonate hydrate, zinc acetate, zinc stearate or zinc diethyldithiocarbamate, most preferably zinc octanoate.

The crude undistilled reaction mixture (PP Base) obtained from the reaction of methyl acrylate with 2,6-di-'butylphenol can be used directly (after stripping of volatile components) without neutralisation or with partial neutralisation with a carboxylic acid.

The methanol by-product of the transesterification reaction can be removed by solvent sparging (e.g. cyclohexane), nitrogen sparging and/or application of vacuum. As the transesterification reaction described herein is an equilibrium reaction, it is important to efficiently remove methanol by-product in order to limit the reverse reaction.

The present invention is also tetrakis[3-(3,5-di-tert-butyl-4-hydroxy phenyl)propionyl oxymethyl]methane wherever prepared or produced by the process herein described and claimed.

In a modification of the process according to the invention, a $C_2$ to $C_4$ alkyl (preferably ethyl) ester other than methyl-(3, 5-di-tert-butyl-4-hydroxy phenol) propionate is used as a starting material for the transesterification reaction.

The new catalyst system of the invention is designed to avoid the use of organo-tin catalysts and their associated problems.

The following Examples will serve to illustrate the invention.

EXAMPLE 1

PP Base (277 g, 15% excess), pentaerythritol (28 g) and lithium hydroxide monohydrate (0.15 g, 1.7 mol %/Penta) were charged to 500 ml litre 4-necked flask equipped with a stirrer, thermometer, pump inlet and distillation head fitted to a condenser, which in turn goes to a liquid-liquid exchanger containing water and cyclohexane. A pump is used to circulate the cyclohexane from the exchanger back into the reactor at a rate of about 0.4 g cyclohexane/PP Base g per hour, thus allowing continual distillation of cyclohexane+by-product methanol (the latter being extracted into water by the exchanger).

The reaction mass was heated to 175° C. with distillation of cyclohexane and methanol. Two shots of zinc octanoate (0.448 g, 0.6 mol %/Penta) were added after 5 and 12 h. Samples were taken at regular intervals and analysed by HPLC, with results given in area % in the Table below.

| Time (hrs) | PP Acid | Disub | Tris | Anox 20 | PP Base |
|---|---|---|---|---|---|
| 3 | 0.4 | 7.9 | 31.2 | 27.3 | 32.7 |
| 5 | 0.4 | 5.0 | 27.5 | 38.6 | 28.0 |
| 7 | 0.4 | 1.9 | 19.7 | 56.2 | 21.5 |
| 9 | 0.4 | 0.9 | 13.1 | 66.8 | 18.4 |
| 12 | 0.5 | 0.6 | 7.8 | 74.2 | 16.1 |
| 14 | 0.5 | 0.3 | 4.9 | 78.8 | 15.0 |
| 16 | 0.5 | 0.3 | 3.7 | 80.2 | 14.7 |

After purification (dilution with cyclohexane, washing, separation of the aqueous layer, drying and crystallisation from cyclohexane), the colour of the Anox 20 final product was found to be APHA 6.

EXAMPLE 1a

Example 1 was repeated but with a reduced excess of PP Base (260 g, 8% excess), and with just one shot of zinc octanoate (0.9 g, 1.2 mol %/Penta) after 5 h.

The results are provided in the Table below.

| Time (hrs) | PP Acid | Disub | Tris | Anox 20 | PP Base |
|---|---|---|---|---|---|
| 3 | 0.4 | 5.8 | 29.5 | 39.4 | 24.0 |
| 5 | 0.4 | 4.7 | 27.2 | 45.4 | 21.5 |
| 7 | 0.4 | 2.2 | 22.0 | 56.8 | 17.6 |
| 9 | 0.4 | 1.4 | 16.9 | 65.1 | 15.5 |
| 12 | 0.5 | 0.8 | 11.7 | 73.5 | 12.7 |
| 14 | 0.6 | 0.5 | 8.5 | 77.9 | 11.6 |
| 19 | 0.7 | 0.3 | 5 | 80.0 | 10.9 |

After purification, the colour of the Anox 20 final product was found to be APHA 5

COMPARATIVE EXAMPLE 1

Example 1 was repeated but with lithium hydroxide monohydrate (0.44 g, 5 mol %/Penta) dosed in eight 0.055 g shots at 2 h intervals. The time taken to reach a level of 5% Tris (the point at which the reaction is regarded as complete, and ready to go into the purification stage) was found to be 21 h.

After purification, the colour of the Anox 20 final product was found to be APHA 14

COMPARATIVE EXAMPLE 1a

Comparative Example 1 was repeated but with lithium hydroxide monohydrate (0.44 g, 5 mol %/Penta) added all at the beginning of the reaction. The time taken to reach a level of 5% Tris was found to be 28 h.

After purification, the colour of the Anox 20 final product was found to be APHA 20

COMPARATIVE EXAMPLE 1b

Comparative example 1 was repeated but with lithium hydroxide monohydrate (0.15 g, 1.7 mol %/Penta) and zinc octanoate (0.9 g, 1.2 mol %/Penta) added together at the start. The time taken to reach a level of 5% Tris was found to be 27 h.

After purification, the colour of the Anox 20 final product was found to be APHA 16

These results are summarised in the following Table to illustrate the benefits of the inventive catalyst system.

| Example | PP Base excess (%) | LiOH•H₂O | Zn octanoate | Time to 5% Tris (h) | APHA |
|---|---|---|---|---|---|
| 1 | 15 | 1.7 mol % at start | 0.6 mol % after 5 h and 12 h | 14 | 6 |
| 1a | 8 | 1.7 mol % at start | 1.2 mol % after 5 h | 19 | 5 |
| Comparative 1 | 15 | 5 mol % dosed over 16 h | None | 21 | 14 |
| Comparative 1a | 15 | 5 mol % at the start | None | 28 | 20 |
| Comparative 1b | 15 | 1.7 mol % at start | 1.2 mol % at start | 27 | 16 |

COMPARATIVE EXAMPLE 2

PP Base (247 g, 15% excess), pentaerythritol (25 g) and lithium acetate (0.75 g, 3 mol %/PE) were charged to 500 ml litre 4-necked flask equipped with a stirrer, thermometer, pump inlet and distillation head fitted to a condenser, which in turn goes to a liquid-liquid exchanger containing water and cyclohexane. A pump is used to circulate the cyclohexane from the exchanger back into the reactor at a rate of about 1.6 g/min, thus allowing continual distillation of cyclohexane+ by-product methanol (the latter being extracted into water by the exchanger).

The reaction mass was heated to 180° C. with distillation of cyclohexane and methanol. Samples were taken at regular intervals and analysed by HPLC, with results given in area % in the Table below.

| Time (hrs) | PP Acid | Disub | Tris | De-butyl | A20 | PP Base |
|---|---|---|---|---|---|---|
| 2 | 0.37 | 10.29 | 29.95 | 0.09 | 16.36 | 40.86 |
| 4 | 0.39 | 5.2 | 28.38 | 0.2 | 32.67 | 31.54 |
| 6 | 0.41 | 2.83 | 23.81 | 0.41 | 44.49 | 26.43 |
| 23 | 0.44 | 0.33 | 9.54 | 0.66 | 68.83 | 18.34 |
| 47 | 0.47 | 0.08 | 4.98 | 0.92 | 75.39 | 16.02 |

COMPARATIVE EXAMPLE 3

As Comparative Example 2, but instead zinc octanoate (2.9 g, 3 mol %/PE) was used as catalyst with the following results.

| Time (hrs) | PP Acid | Disub | Tris | De-butyl | A20 | PP Base |
|---|---|---|---|---|---|---|
| 1 | 0.02 | 4.10 | 0.62 | 0.00 | 0.17 | 89.61 |
| 2 | 0.00 | 10.77 | 3.36 | 0.01 | 0.15 | 77.15 |
| 3 | 0.00 | 15.63 | 7.05 | 0.02 | 0.40 | 68.47 |
| 4 | 0.00 | 18.25 | 11.95 | 0.01 | 0.88 | 62.05 |
| 5 | 0.00 | 18.28 | 16.29 | 0.02 | 1.52 | 58.33 |
| 22.8 | 0.00 | 3.90 | 30.64 | 0.71 | 28.69 | 33.22 |

EXAMPLE 2

As Comparative Example 2, but with lithium acetate (0.75 g, 3 mol %/PE) added at the beginning, and zinc acetate (1.43 g, 3 mol %/PE) added after 4 h at 180° C., with the following results.

| Time (hrs) | PP Acid | Disub | Tris | De-butyl | A20 | PP Base |
|---|---|---|---|---|---|---|
| 1 | 0.28 | 16.88 | 18.49 | 0.04 | 3.39 | 55.53 |
| 2 | 0.40 | 10.44 | 30.22 | 0.40 | 15.32 | 40.53 |
| 3 | 0.47 | 6.96 | 30.02 | 0.55 | 24.96 | 34.75 |
| 4 | 0.47 | 5.34 | 28.65 | 0.63 | 30.51 | 32.08 |
| 5 | 0.55 | 2.92 | 24.74 | 0.77 | 40.26 | 28.03 |
| 6 | 0.66 | 1.83 | 20.54 | 0.87 | 47.36 | 25.65 |
| 22.3 | 02.21 | 0.02 | 2.07 | 1.29 | 74.53 | 15.27 |

EXAMPLE 3

As Example 2, but with a reduced amount of PP Base (227.4 g, 8% excess) used.

| Time (hrs) | PP Acid | Disub | Tris | De-butyl | A20 | PP Base |
|---|---|---|---|---|---|---|
| 1 | 0.30 | 17.88 | 21.13 | 0.05 | 4.42 | 50.82 |
| 2 | 0.41 | 12.02 | 31.63 | 0.41 | 15.92 | 36.66 |
| 3 | 0.60 | 6.72 | 29.12 | 0.75 | 33.28 | 27.04 |
| 4 | 0.67 | 6.44 | 29.06 | 0.84 | 36.25 | 26.24 |
| 5 | 0.81 | 3.48 | 26.25 | 0.94 | 43.25 | 22.47 |
| 6 | 0.89 | 2.36 | 22.82 | 1.09 | 49.23 | 20.30 |
| 7 | 1.06 | 1.61 | 19.69 | 1.22 | 55.20 | 17.47 |
| 23.3 | 2.78 | 0.08 | 4.58 | 1.67 | 76.42 | 8.86 |

EXAMPLE 4

As Example 2, but with a lower amount of zinc acetate (0.72 g, 1.5 mol %/PE) used.

| Time (hrs) | PP Acid | Disub | Tris | De-butyl | A20 | PP Base |
|---|---|---|---|---|---|---|
| 1 | 0.24 | 15.87 | 22.86 | 0.07 | 5.41 | 51.39 |
| 2 | 0.37 | 9.59 | 30.26 | 0.41 | 17.29 | 39.67 |
| 3 | 0.40 | 6.75 | 29.66 | 0.51 | 25.16 | 35.31 |
| 4 | 0.38 | 5.15 | 28.12 | 0.58 | 30.92 | 32.63 |
| 5 | 0.52 | 3.18 | 24.96 | 0.69 | 39.20 | 28.99 |
| 6 | 0.61 | 1.90 | 20.72 | 0.80 | 46.75 | 26.54 |
| 23.3 | 1.64 | 0.02 | 2.47 | 1.23 | 74.42 | 15.68 |

EXAMPLE 5

As Example 4, but with a lower amount of lithium acetate (0.38 g, 1.5 mol %/PE) used.

| Time (hrs) | PP Acid | Disub | Tris | De-butyl | A20 | PP Base |
|---|---|---|---|---|---|---|
| 1 | 0.11 | 16.39 | 14.71 | 0.03 | 2.32 | 60.52 |
| 2 | 0.14 | 12.51 | 28.61 | 0.13 | 11.81 | 43.90 |
| 3 | 0.21 | 9.02 | 30.41 | 0.24 | 19.56 | 38.24 |
| 4 | 0.23 | 6.94 | 29.83 | 0.47 | 25.34 | 35.01 |
| 5 | 0.29 | 4.48 | 28.21 | 0.56 | 32.66 | 31.46 |
| 6 | 0.30 | 2.97 | 25.29 | 0.66 | 40.88 | 27.33 |
| 22.5 | 1.03 | 0.01 | 1.84 | 1.16 | 75.42 | 16.66 |

EXAMPLE 6

As Example 2, but with lithium acetate (0.2 g, 1.5 mol %/PP base) added at the beginning and zinc acetylacetonate (0.73 g, 1.5 mol %/PP base) added after 4 h, with the following results obtained.

| Time (hrs) | PP Acid | Disub | Tris | De-butyl | A20 | PP Base |
|---|---|---|---|---|---|---|
| 3 | 0.3 | 5.0 | 27.0 | 0.6 | 28.7 | 35.8 |
| 4 | 0.3 | 2.9 | 23.4 | 0.7 | 39.3 | 31.0 |
| 6 | 0.4 | 0.5 | 10.9 | 1.0 | 61.7 | 20.9 |
| 10 | 0.4 | 0 | 1.4 | 1.1 | 75.1 | 18.7 |

EXAMPLES 7-23

A Radleys Carousel 6 Place Reaction Station, with 250 ml flasks connected to water-pump vacuum in order to facilitate methanol removal was used to screen different catalysts for the reaction of pentaerythritol (2.8 g) and PP Base (27.2 g, 13% excess) at a reaction temperature of 180° C. Catalysts were used at a total loading of 3 mol %/PP Base (where two catalysts were used, each was added at 1.5 mol % loading). Where two catalysts were used, the $2^{nd}$ catalyst was added after 4 h. Anox 20 content is given by HPLC area % of the final product mixture.

The results obtained are summarised in the following table

| Example | Catalyst-1 | Catalyst-2 | Time (h) | Anox 20 (area %) |
|---|---|---|---|---|
| 7 | Lithium hydroxide | None | 20 | 61 |
| 8 | Lithium acetate | None | 20 | 58 |
| 8a | Lithium acetate | None | 24 | 60 |
| 9 | Lithium methoxide | None | 20 | 68 |
| 10 | Lithium acetate | Zinc acetate | 20 | 70 |
| 10a | Lithium acetate | Zinc acetate | 20 | 68 |
| 11 | Lithium methoxide | Zinc acetate | 20 | 74 |
| 12 | Lithium methoxide | Zinc stearate | 17 | 78 |
| 13 | Lithium acetate | Zinc stearate | 24 | 72 |
| 14 | Lithium acetate | Zinc p-toluene sulphonate | 24 | 68 |
| 15 | Lithium acetate | Zinc octanoate | 24 | 79 |
| 16 | Lithium hydroxide | Zinc octanoate | 24 | 81 |
| 17 | Lithium acetate | Zinc diethyldithio carbamate | 22 | 77 |
| 18 | Lithium | Zinc acetate | 22 | 70 |
| 19 | Calcium hydride | None | 24 | 34 |
| 20 | Gallium acetylacetonate | None | 24 | 0.2 |
| 21 | Calcium hydride | Gallium acetylacetonate | 24 | 70 |
| 22 | Lithium acetate | Lanthanum acetylacetonate | 24 | 67 |
| 23 | Lithium acetate | Manganese acetate | 24 | 74 |

Whilst we do not wish to be bound by the following theory, we believe that the transesterification process of the present invention operates as described below and as illustrated in the following pages 12(a) and 12(b) of schematic reaction drawings.

The reaction of pentaerythritol (Penta) with methyl (3,5-di-tert-butyl-4-hydroxyphenyl)propionate (PP Base) gives first a mono-substituted product (MONO), subsequent reaction of MONO with a $2^{nd}$ molecule of PP Base gives the di-substituted product (DI), reaction of DI with a $3^{rd}$ molecule of PP Base gives the tri-substituted product (TRIS). Finally, reaction of TRIS with a $4^{th}$ molecule of PP Base gives Anox 20.

The use of Lewis acid catalysts, and especially bivalent, trivalent and tetravalent metal species, is ineffective when used from the start of the reaction. This is because of the deactivation of the catalysts by complexation of the metal ions through chelation of the metal species by the poly hydroxy compounds, PENTA, MONO and DI.

Basic catalysts, especially compounds of Group 1A (alkali) metals and Group IIA (alkaline earth) metals are used to promote the first stages of the reaction: PENTA to MONO to DI to TRIS and partial conversion of the TRIS to ANOX 20.

When the 'chelating intermediates' MONO and DI have reached a sufficiently low level e.g. <20% DI and preferably <10% DI, within the reaction mixture the Lewis acid catalyst can be most effectively added to accelerate the reaction.

The choice of timing of addition can be optimised through normal experimentation of one skilled in the art, to minimise reaction time and colour and maximise conversion.

We are of the opinion that the classic Lewis acids described in the prior art for use in transesterification processes do not work well when used alone in the transesterification process of the present invention due to deactivation by the pentaerythritol intermediates of the reaction. This is because of the positioning of the OH groups of the pentaerythritol so that chelation of the various metals (e.g. Mg, Zn, Al) is favourable. Basic catalysts can be used (e.g. LiOH) but they suffer from the disadvantage of causing increased colour formation (base catalyses oxidation reactions that cause discolouration) and the stronger the base the greater is the risk of discolouration. Lewis acids do not catalyse the discolouration reactions. Also, the reaction slows down as the OH groups of the pentaerythritol are reacted in sequence. By using a base to carry out up to the first 60 to 75% of the reaction, then adding a Lewis acid allows minimum use of base, maximum rate enhancement for minimum colour formation and overcomes the problems of deactivation of the Lewis acid cation species by converting the intermediate poly-OH species so that only small amounts remain (typically less than 10% di-substituted by-products). In short, the key to success of the process of the invention is the addition of the base catalyst at the beginning of the reaction and adding the Lewis acid catalyst only after the chelating/deactivating intermediates have been reduced below a certain level.

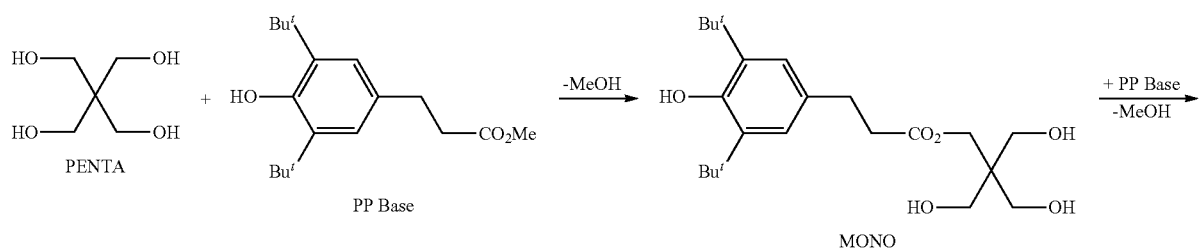

-continued

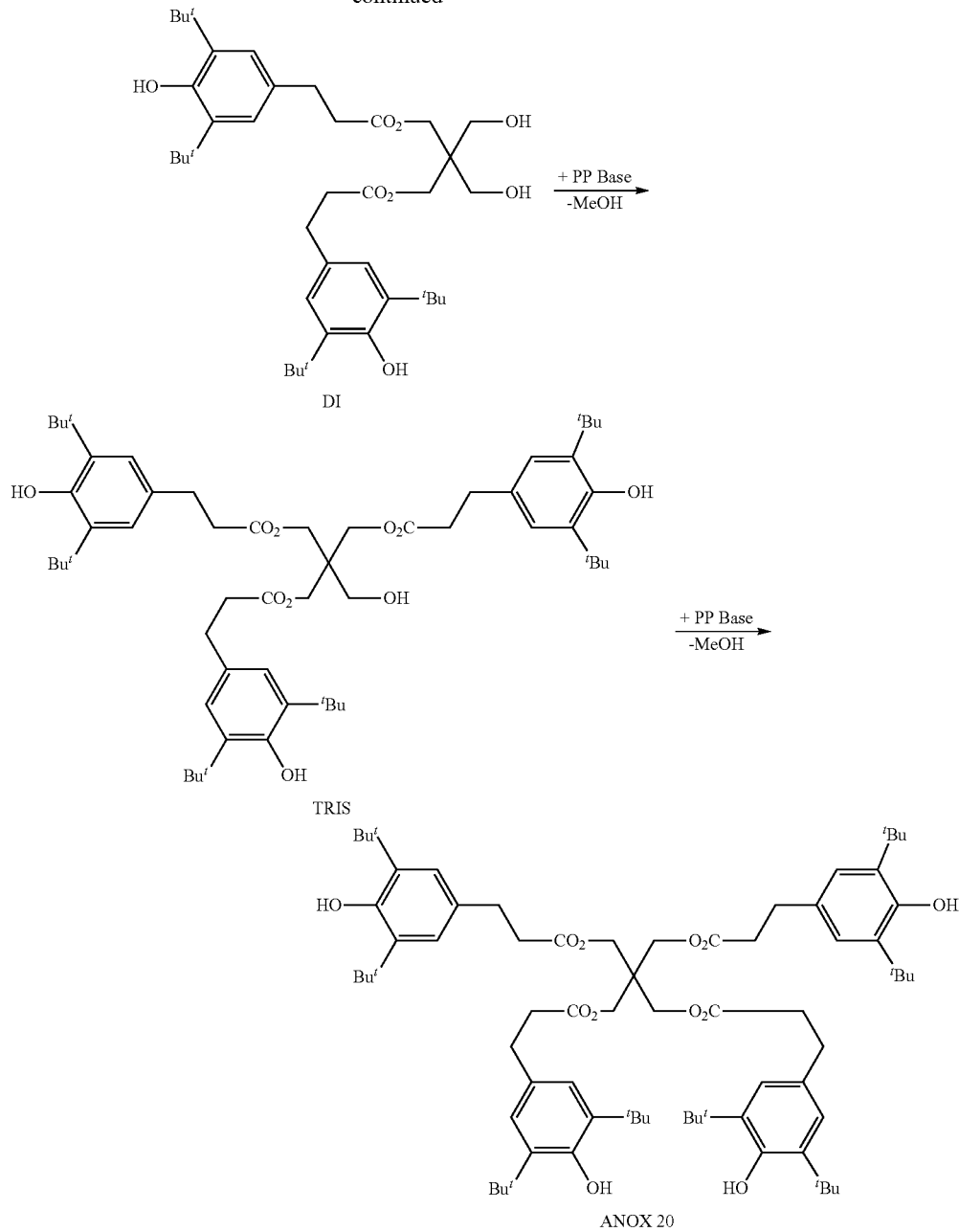

DI

TRIS

ANOX 20

There now follows a list of possibly first and second stage catalysts.
Examples (Non-Limiting) of Group 1A Compounds for Basic/Neutral Catalysts (Non-Limiting)
lithium hydroxide
lithium hydroxide monohydrate
lithium metal
lithium acetate
lithium hexanoate
lithium octanoate
lithium methoxide
lithium isopropoxide
lithium hydride
lithium triethyl borohydride
lithium amide
sodium hydroxide
sodium methoxide
sodium hydride
sodium acetate
sodium triethyl borohydride
potassium hydroxide
potassium acetate
potassium t-butoxide
potassium fluoride
Examples (Non-Limiting) of Group IIA Compounds as Basic Catalysts
calcium hydroxide
calcium oxide
calcium hydride Preferred are lithium hydroxide, lithium methoxide, lithium hydride and lithium acetate Most preferred is lithium hydroxide and lithium hydroxide monohydrate Examples (Non-Limiting) of Lewis Acids:
zinc octanoate
zinc acetate
zinc acetylacetonate hydrate
zinc stearate
zinc p-toluene sulphonate
zinc naphthenate
zinc diethyldithiocarbamate
manganese (II) acetate
manganese (II) acetylacetonate
manganese (III) acetyl acetonate
cobalt (II) acetate
cobalt (II) acetylacetonate
nickel acetate tetrahydrate
nickel acetylacetonate
nickel stearate
calcium acetate
aluminium phenate
aluminium isopropoxide
aluminium acetylacetonate
titanium tetrabutoxide
titanium oxide acetylacetonate
titanium isopropoxide bis(acetylacetonate)
gallium acetate
lanthanum acetate
lanthanum acetyl acetonate. hydrate
yttrium 2-ethylhexanoate
yttrium acetate dihydrate
zirconium (IV) acetylacetonate
vanadium acetylacetonate Preferred are zinc octanoate, zinc acetylacetonate hydrate, zinc acetate, zinc stearate and zinc diethyldithiocarbamate Most preferred is zinc octanoate

The invention claimed is:

1. A transesterification process for the preparation of tetrakis[3-(3,5-di-tertbutyl-4-hydroxy phenyl)propionyl oxymethyl]methane by the reaction of methyl-(3,5-di-tert-butyl-4-hydroxy phenyl)propionate ester with pentaerythritol wherein the reaction takes place in the presence of an ester exchange catalyst combination consisting of (a) at least one basic or neutral catalyst and (b) at least one metal compound capable of behaving as a Lewis acid being different from the basic or neutral catalyst and wherein the reaction is conducted through a first stage in which only the at least one basic or neutral catalyst is present in the reaction mixture followed by a second stage which commences with the addition of Lewis acid catalyst to the reaction mixture when the amount of di-substituted intermediate product contained within the reaction mixture is has been reduced to less than 20 area % analyzed by HPLC.

2. A process as claimed in claim 1 wherein the Lewis acid is added to the intermediate reaction mixture when the amount of di-substituted intermediate product contained within the reaction mixture is less than 10 area %.

3. A process as claimed in claim 1 wherein the basic or neutral catalyst is selected from a group Ia alkali metal, a group Ia alkali metal compound or a group IIa alkaline earth compound.

4. A process as claimed in claim 3 wherein the basic or neutral catalyst is lithium hydroxide, lithium hydroxide monohydrate, lithium methoxide, lithium hydride, lithium acetate or lithium amide.

5. A process as claimed in claim 4 wherein the basic catalyst is lithium hydroxide or lithium hydroxide monohydrate.

6. A process as claimed in claim 1 wherein the metal compound capable of behaving as a Lewis acid is a compound of a group Ib metal, a group IIa metal, a group IIb metal, a group IIIb metal, a group IVb metal, a group Vb metal, a transition metal, a lanthanide or an actinide.

7. A process as claimed in claim 6 wherein the Lewis acid catalyst is zinc acetyl acetonate hydrate, zinc acetate, zinc stearate or zinc diethyldithiocarbamate.

8. A process as claimed in claim 1 wherein the crude undistilled reaction mixture from the preparation of the methyl-(3,5-di-tertbutyl-4-hydroxy phenyl)propionate is used without neutralization or is used with partial neutralization with a carboxylic acid in the transesterification process.

9. A process as claimed in claim 1 wherein the methanol by-product of the transesterification reaction is removed by solvent sparging, nitrogen sparging and/or application of vacuum.

10. A modification of the process as claimed in claim 1 in which a $C_2$ to $C_4$ alkyl ester other than methyl-(3,5-di-tert-butyl-4-hydroxy phenyl)propionate is used as a starting material for the transesterification reaction.

11. The process of claim 1 wherein the at least on metal compound capable of behaving as a Lewis acid is selected from the group consisting of a group Ib metal or compound thereof, a group IIa metal or compound thereof, a group IIIb metal or compound thereof, a group IVb metal or compound thereof, a group Vb metal of compound thereof, a lanthanide or compound thereof, an actinide or compound thereof, zinc stearate, zinc p-toluene sulphonate, zinc acetylacetonate hydrate, zinc naphthenate, zinc diethyldithiocarbamate, manganese (II) acetate, manganese (II) acetylacetonate, manganese (III) acetylacetonate, cobalt (II) acetate, cobalt (II) acetylacetonate, nickel acetate tetrahydrate, nickel acetylacetonate, nickel stearate, aluminum phenate, aluminum isopropoxide, aluminum acetylacetonate and gallium acetate.

12. A transesterification process for the preparation of tetrakis[3-(3,5-di-tertbutyl-4-hydroxy phenyl)propionyl oxymethyl]methane by the reaction of methyl-(3,5-di-tert-butyl-4-hydroxy phenyl)propionate ester with pentaerythritol wherein the reaction takes place in the presence of an ester exchange catalyst combination consisting of (a) at least one basic or neutral catalyst and (b) at least one metal compound capable of behaving as a Lewis acid being different from the basic or neutral catalyst and being selected from the group consisting of a group Ib metal or compound thereof, a group IIa metal or compound thereof, a group IIIb metal or compound thereof, a group IVb metal or compound thereof, a group Vb metal of compound thereof, a lanthanide or compound thereof, an actinide or compound thereof, zinc stearate, zinc p-toluene sulphonate, zinc acetylacetonate hydrate, zinc naphthenate, zinc diethyldithiocarbamate, manganese (II) acetate, manganese (II) acetylacetonate, manganese (III) acetylacetonate, cobalt (II) acetate, cobalt (II) acetylacetonate, nickel acetate tetrahydrate, nickel acetylacetonate, nickel stearate, aluminum phenate, aluminum isopropoxide, aluminum acetylacetonate and gallium acetate, and wherein the reaction is conducted through a first stage in which only the at least one basic or neutral catalyst is present in the reaction mixture followed by a second stage which commences with the addition of the at least one metal compound capable of behaving as a Lewis acid to the reaction mixture when the amount of di-substituted intermediate product contained within the reaction mixture is has been reduced to less than 20 area % analyzed by HPLC.

13. A transesterification process for the preparation of tetrakis[3-(3,5-di-tertbutyl-4-hydroxy phenyl)propionyl oxymethyl]methane by the reaction of a C2 to C4 alkyl ester other than methyl-(3,5-di-tert-butyl-4-hydroxy phenyl)propionate ester with pentaerythritol wherein the reaction takes place in the presence of an ester exchange catalyst combination consisting of (a) at least one basic or neutral catalyst and (b) at least one metal compound capable of behaving as a Lewis acid being different from the basic or neutral catalyst and wherein the reaction is conducted through a first stage in which only the at least one basic or neutral catalyst is present in the reaction mixture followed by a second stage which commences with the addition of Lewis acid catalyst to the reaction mixture when the amount of di-substituted intermediate product contained within the reaction mixture is has been reduced to less than 20 area % analyzed by HPLC.

14. The process of claim 13 wherein the at least on metal compound capable of behaving as a Lewis acid is selected from the group consisting of a group Ib metal or compound thereof, a group IIa metal or compound thereof, a group IIIb metal or compound thereof, a group IVb metal or compound thereof, a group Vb metal of compound thereof, a lanthanide or compound thereof, an actinide or compound thereof, zinc stearate, zinc p-toluene sulphonate, zinc acetylacetonate hydrate, zinc naphthenate, zinc diethyldithiocarbamate, manganese (II) acetate, manganese (II) acetylacetonate, manganese (III) acetylacetonate, cobalt (II) acetate, cobalt (II) acetylacetonate, nickel acetate tetrahydrate, nickel acetylacetonate, nickel stearate, aluminum phenate, aluminum isopropoxide, aluminum acetylacetonate and gallium acetate.

* * * * *